(12) United States Patent
Rath

(10) Patent No.: US 9,380,983 B2
(45) Date of Patent: Jul. 5, 2016

(54) METHOD AND SYSTEM FOR FAIL-PROOF PATIENT MONITORING

(71) Applicant: Wipro Limited, Bangalore (IN)

(72) Inventor: Satish Prasad Rath, Bangalore (IN)

(73) Assignee: Wipro Limited, Bangalore (IN)

( * ) Notice: Subject to any disclaimer, the term of this patent is extended or adjusted under 35 U.S.C. 154(b) by 183 days.

(21) Appl. No.: 14/175,724

(22) Filed: Feb. 7, 2014

(65) Prior Publication Data

US 2015/0182174 A1 Jul. 2, 2015

(30) Foreign Application Priority Data

Dec. 27, 2013 (IN) .......................... 6130/CHE/2013

(51) Int. Cl.

| | |
|---|---|
| G08B 19/00 | (2006.01) |
| G08B 21/00 | (2006.01) |
| H04Q 9/00 | (2006.01) |
| G08C 19/22 | (2006.01) |
| G08B 1/08 | (2006.01) |
| A61B 5/00 | (2006.01) |
| A61B 5/0205 | (2006.01) |
| G06F 19/00 | (2011.01) |
| A61B 5/021 | (2006.01) |
| A61B 5/024 | (2006.01) |
| A61B 5/08 | (2006.01) |
| A61B 5/01 | (2006.01) |

(52) U.S. Cl.
CPC ............ *A61B 5/746* (2013.01); *A61B 5/02055* (2013.01); *A61B 5/7203* (2013.01); *A61B 5/7221* (2013.01); *A61B 5/7282* (2013.01); *A61B 5/743* (2013.01); *G06F 19/3418* (2013.01); *A61B 5/0022* (2013.01); *A61B 5/01* (2013.01); *A61B 5/021* (2013.01); *A61B 5/024* (2013.01); *A61B 5/0816* (2013.01); *A61B 2560/0276* (2013.01)

(58) Field of Classification Search
None
See application file for complete search history.

(56) References Cited

U.S. PATENT DOCUMENTS

| | | | |
|---|---|---|---|
| 5,036,852 A | 8/1991 | Leishman | |
| 6,612,985 B2 | 9/2003 | Eiffert et al. | |
| 2008/0281168 A1* | 11/2008 | Gibson | ............... A61B 5/0205 600/301 |
| 2008/0281169 A1* | 11/2008 | Akkermans | .............. A61B 5/00 600/301 |
| 2011/0060215 A1* | 3/2011 | Tupin, Jr. | ............. A61B 5/0507 600/425 |

* cited by examiner

*Primary Examiner* — Firmin Backer
*Assistant Examiner* — Jerold Murphy
(74) *Attorney, Agent, or Firm* — LeClairRyan, a Professional Corporation

(57) ABSTRACT

This disclosure relates generally to patient monitoring techniques, and more specifically to a method and a system to reduce false alarms generated by the patient monitoring system, the false alarms being associated with clinical condition of the patient. Disclosed herein is a patient monitoring method that includes monitoring one or more clinical parameters associated with condition of a patient, identifying a clinical condition based on deviation of the monitored one or more clinical parameters from corresponding one or more first predefined criteria, determining a status associated with one or more devices that monitor the deviated one or more clinical parameters, and generating a clinical alert based on the determined status not indicating an error by the one or more devices.

19 Claims, 5 Drawing Sheets

METHOD AND SYSTEM FOR FAIL-PROOF PATIENT MONITORING

This application claims the benefit of Indian Patent Application Filing Number 6130/CHE/2013, filed on Dec. 27, 2013, which is hereby incorporated by reference in its entirety.

FIELD

This disclosure relates generally to patient monitoring techniques, and more specifically to a method and system to reduce false clinical alerts triggered by the patient monitoring system, the false clinical alerts being associated with a clinical condition of a patient.

BACKGROUND

Various technological improvements in recent times have made monitoring of patients easy and useful. The monitoring of patients by one or more devices means real-time tracking of patient data which otherwise is not feasible to be conducted by a human care-giver, like a nurse or an attending physician. Such automated patient monitoring system has also made it possible to simultaneously monitor lot of patients without actually physically visiting them. Now, in case the patient data or vitals deviate from predefined criteria, the patient monitoring system automatically generates alerts to inform concerned person of the condition of the patient. The care-giver or a specialist then takes next measures in accordance with the reported data. The predefined criteria may be a set of defined clinical guidelines.

Such advanced automatic patient monitoring data providing improved patient care is based on fundamental premise that the patient data that is continuously reported is deemed accurate, and therefore the physician can blindly rely upon such data to decide next course of action or mediation for the patient. However, in some instances, the monitoring system may generate false alarms regarding the clinical condition of a patient due to some error or fault of the devices within the patient monitoring system.

It may be a matter of concern if the patient monitoring systems generates false alerts/alarms which are solely relied upon by the physician or the care-giver to decide the subsequent course of medication or patient care. Additionally, presently available patient monitoring systems suffer from lack of sufficient measures to prevent failure of the devices within the patient monitoring system which in turn has serious impact on delivering a sustained and safe patient care by the patient monitoring system.

SUMMARY

Disclosed herein is a patient monitoring method that includes: monitoring one or more clinical parameters associated with a patient; identifying a clinical condition based on deviation of the monitored one or more clinical parameters from a corresponding one or more first predefined criteria; determining a status associated with one or more devices that monitor the deviated one or more clinical parameters; and generating a clinical alert based on the determined status not indicating an error in the one or more devices.

In an aspect of the present disclosure, a patient monitoring system includes a memory, a processor coupled to the memory storing processor executable instructions which when executed by the processor causes the processor to instruct each of the one or more devices in communication with the one or more devices to monitor an associated clinical parameter, identify a clinical condition based on deviation of the monitored one or more clinical parameters from corresponding one or more first predefined criteria, determine a status associated with one or more devices monitoring the deviated one or more clinical parameters; and generate a clinical alert based on the status not indicating an error in the one or more devices.

It is to be understood that both the foregoing general description and the following detailed description are exemplary and explanatory only and are not restrictive of the present disclosure, as claimed.

DETAILED DESCRIPTION

Now, exemplary embodiments of the present disclosure will be described with reference to the accompanying drawings. Wherever possible, the same reference numbers will be used throughout the drawings to refer to the same or like parts. While exemplary embodiments and features are described herein, modifications, adaptations, and other implementations are possible, without departing from the spirit and scope of the disclosure. Accordingly, the following detailed description does not limit the subject matter. Instead, the proper scope of the subject matter is defined by the appended claims.

Figure 1:
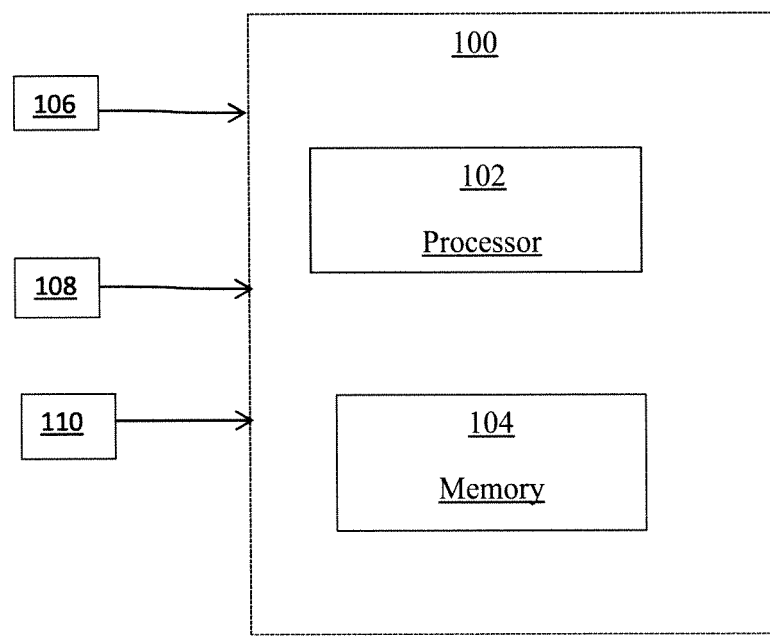
FIG. 1 illustrates an exemplary patient monitoring system for preventing triggering of false alerts in accordance with some embodiments of the present disclosure.

FIG. 1 illustrates an exemplary patient monitoring system 100 to prevent triggering of false alerts in accordance with some embodiments of the present disclosure. The patient monitoring system 100 comprises a processor 102 and a memory 104 in electronic communication with each other. The electronic communication may be wired or wireless. The electronic communication may be through means of a communication network that may include, without limitation, a direct interconnection, local area network (LAN), wide area network (WAN), wireless network (e.g., using Wireless Application Protocol), the Internet, etc.

The processor 102 may instruct one or more devices (106, 108, 110) in communication with the processor 102, to monitor corresponding one or more clinical parameters. The processor 102 detects patient's clinical condition based on deviation of the monitored one or more clinical parameters from a corresponding one or more first predetermined criteria. The one or more first predefined criteria may pertain to a range of values within which the values related to the monitored one or more clinical parameters should lie. Therefore, the values related to the monitored one or more clinical parameters should not go below a predefined lower threshold or above a predefined upper threshold. For example, the range of values within which the blood pressure of a patient should lie is 80-120 mmHg. The alarm or clinical alert may trigger when the BP of the patient falls below 80 mmHg or goes beyond 120 mmHg. Further, some of the examples of the one or more clinical parameters may be respiration rate, heart rate, blood pressure, and temperature. Further, the one or more clinical parameters may include position or activity data of the patient, such as lying down, upright, walking, and sitting etc.

Further, the memory 104 is a repository of policy details defining the clinical condition of the patient. Such policy details may be a combination of clinical guidelines and specified standards of health care. Also, the memory 104 may comprise the technical specifications of the one or more devices (106, 108, 110). For example, the one or more devices (106, 108, 110) may be blood pressure (BP) or temperature or ECG device. Further, the memory 104 may comprise values pertaining to signal quality that indicates error free functioning of the patient monitoring system 100. The memory 104 further provides the required benchmarking or threshold for the processor 102 to trigger a clinical alert.

Further, the processor 102 monitors one or more machine parameters related to the one or more devices (106, 108, and 110). There may be deviation of the monitored one or more machine parameters from a corresponding one or more second predefined criteria. For example, the one or more second predefined criteria may comprise a range of values for proper connectivity for transfer of data, optimal operating values for the battery in the one or more devices for their proper functioning, optimal signal to noise ratio. So, the deviation may be loose electrical contacts in the one or more devices (106, 108, 110), low battery in the one or more devices, low signal to noise ratio, and connectivity loss (in continuous data monitoring scenario, connectivity can play spoilsport and conventional patient monitoring systems will generate machine alert on account of inadequate data or improper data). In an exemplary embodiment, the one or more machine parameters that are monitored may comprise electrical contacts in the patient monitoring system 100, battery in the one or more devices (106, 108, 110), signal to noise ratio, and connectivity.

The processor 102 may trigger a clinical alert if there is no deviation of the monitored one or more machine parameters from the corresponding one or more second predefined criteria. The clinical alert would not be triggered if there is deviation of the monitored one or more machine parameters from the corresponding one or more second predefined criteria. The deviation of the monitored one or more machine parameters from the corresponding one or more second predefined criteria would indicate error/fault in the one or more devices (106, 108, 110). To indicate the error/fault in the one or more devices (106, 108, 110), a machine alert is generated. The processor 102 may determine a status associated with the one or more devices (106, 108, 110). If the determined status indicates an error/fault in the one or more devices (106, 108, 110), the processor may not generate a clinical alert. In this case, machine alert is generated. However, if the determined status does not indicate an error/fault in the one or more devices (106, 108, 110), the processor may generate a clinical alert. Therefore, non-generation of the clinical alert when there is fault in the one or more devices (106, 108, 110) would mitigate the problem of triggering of false clinical alerts.

The machine alert, when examined, provides intelligence regarding the following:
   a. Which component is faulty e.g. BP or temperature or ECG device. This information aids in quick solution fixing. As the patient monitoring system 100 is moving towards multi component design, this diagnosis also becomes important.
   b. What is failing out of one or more machine parameters: the battery, the signal, the temperature of the component, the connectivity, the driver and so on. This helps to identify whether the machine alert can be fixed by the end user itself or need intervention by the biomedical department.

The generation of the machine alert helps a nurse to alert the biomedical department for rescue of the system and replace the faulty device with a new one or repair it. Additionally, the generated alert can also be automatically routed to the concerned technical department using the contact details as may be available in the system database. Also, the machine alert can be categorized and/or rated as per defined conditions to determine the nature of the failure or expected failure and its impact on the patient. Accordingly, the alert/alarm can be decided to be forwarded to the appropriate entities.

Data related to the patient and the one or more devices (106, 108, and 110) received by the processor 102 may be stored locally and/or in cloud. Therefore, the data related to patient and devices (106, 108, and 110) may be made available and visible by care-givers who are logging into the patient monitoring system 100 from outside hospital.

Figure 2A:
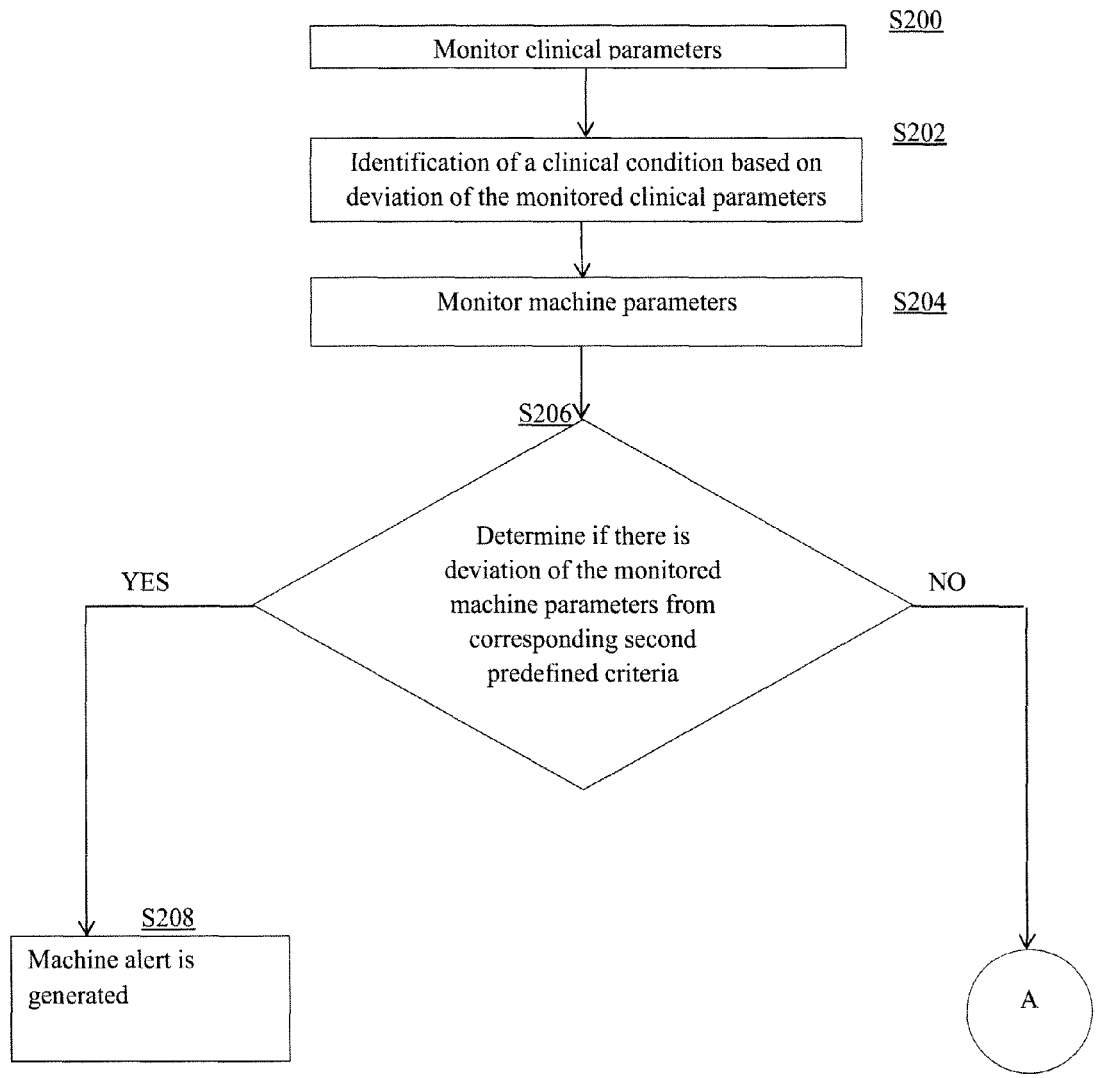
FIGS. 2A and 2B is an exemplary flowchart illustrating a method of preventing triggering of false alerts in accordance with some embodiments of the present disclosure.
Figure 2B:
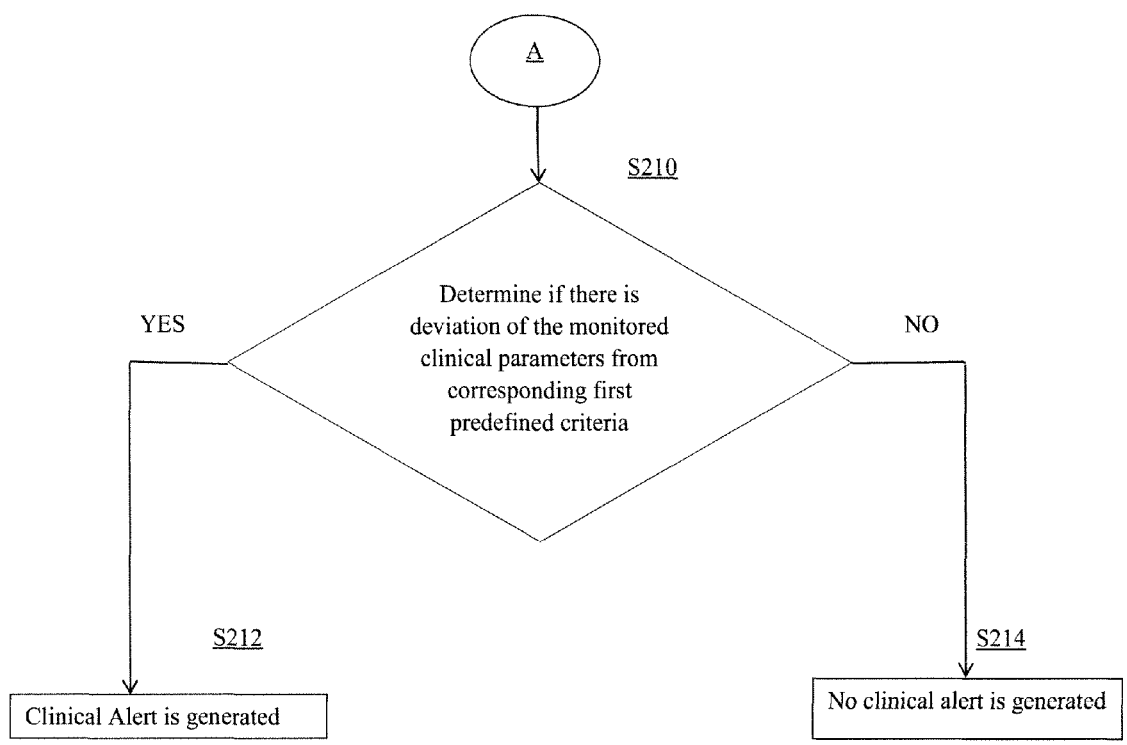

FIGS. 2A and 2B illustrate a flowchart of an example of a method for patient monitoring to prevent triggering of false clinical alerts in accordance with an embodiment of the present disclosure. At step S200, one or more clinical parameters associated with the condition of a patient are monitored. In an exemplary embodiment, the one or more clinical parameters comprise respiration rate, heart rate, blood pressure, and temperature. Further, the one or more parameters may include position and activity data of the patient that indicates whether the patient is lying down, upright, walking, or sitting etc. Further, a clinical condition based on deviation of the monitored one or more clinical parameters from corresponding one or more first predefined criteria is identified (step S202). The one or more first predefined criteria may include predefined range of values within which values related to the monitored one or more clinical parameters should fall. Therefore, the deviation in this case, may be values related to the monitored one or more clinical parameters falling outside the predefined range of values. As explained above, the processor 102 monitors the one or more machine parameters related to the one or more devices (106, 108, 110) (step S204). At step S206, it is determined whether there is deviation of the one or more monitored machine parameters from the one or more corresponding predefined criteria. If answer is YES, machine alert is generated but no clinical alert is generated (step S208). If answer is NO, it is further determined whether there is deviation of the one or more clinical parameters from the corresponding one or more first predefined criteria (S210). If answer is YES, clinical alert is generated (S212). If answer is NO, no clinical alert is generated (S214). The method explained above would reduce the generation of false clinical alerts.

Figure 3:
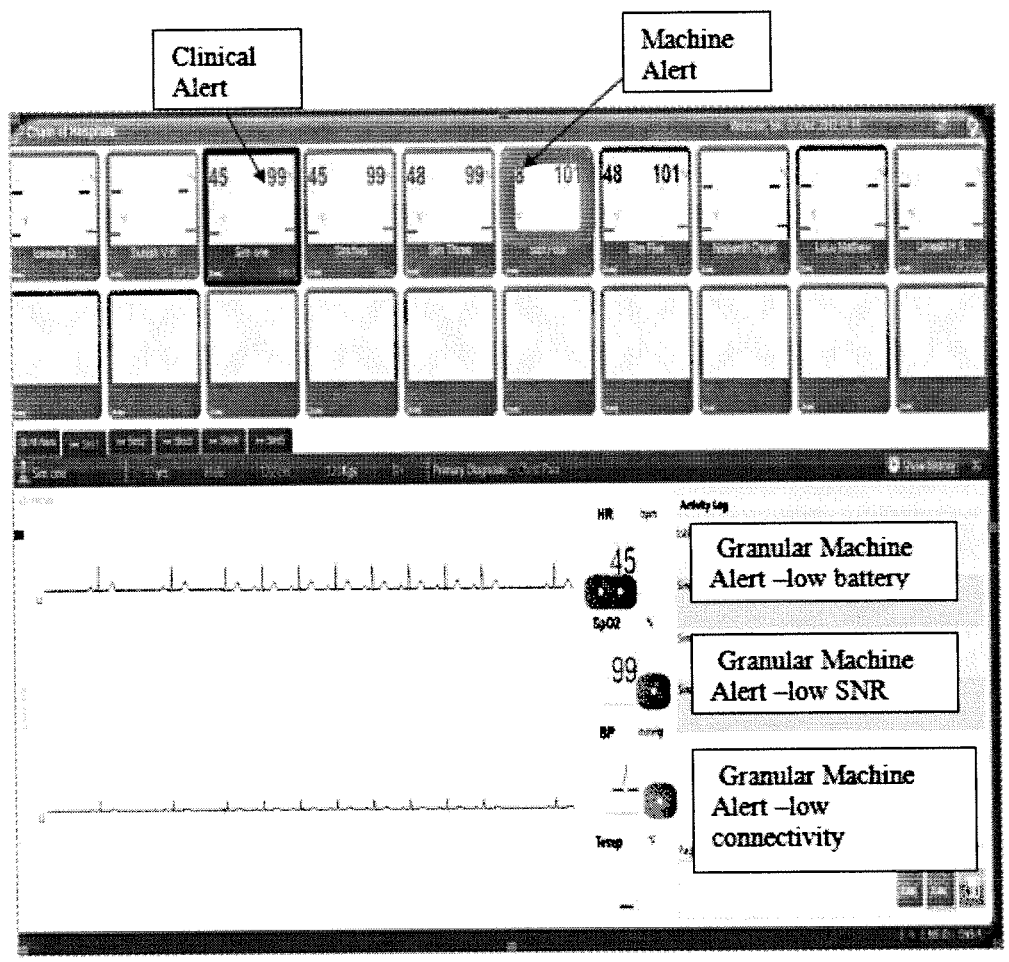
FIG. 3 is an exemplary graphic display illustrating machine alert and clinical alert in accordance with some embodiments of the present disclosure.

FIG. 3 is a graphic display illustrating machine alert and clinical alert in accordance with an embodiment of the present disclosure. The display 110 displays both clinical alert and machine alert. They are flagged with different colors so that they can be easily identified by the care-giver. This offers a great advantage as in existing systems, the care-giver have to manually come to a diagnosis after finding out the machine alert as an artifact of faulty patient monitoring system 100. This is of critical importance when critical care and remote care is required. In critical care, time is important and in remote care, proactive rescue and restoring the one or more devices to their operational status is important. In present disclosure, the one or more machine parameters that can affect or influence the one or more clinical parameters are saved in the reference database 108. The one or more machine parameters are monitored and compared against corresponding one or more second pre-defined criteria for deviation. As and when the one or more machine parameters deviate from the corresponding one or more second pre-defined criteria, machine alert is displayed. When the one or more machine parameters does not deviate, from the corresponding one or more second pre-defined criteria, it is further determined that whether there is deviation of the one or more clinical parameters from the corresponding one or more first predefined criteria. If there is deviation, the clinical alert is triggered and displayed.

Computer System

Figure 4:
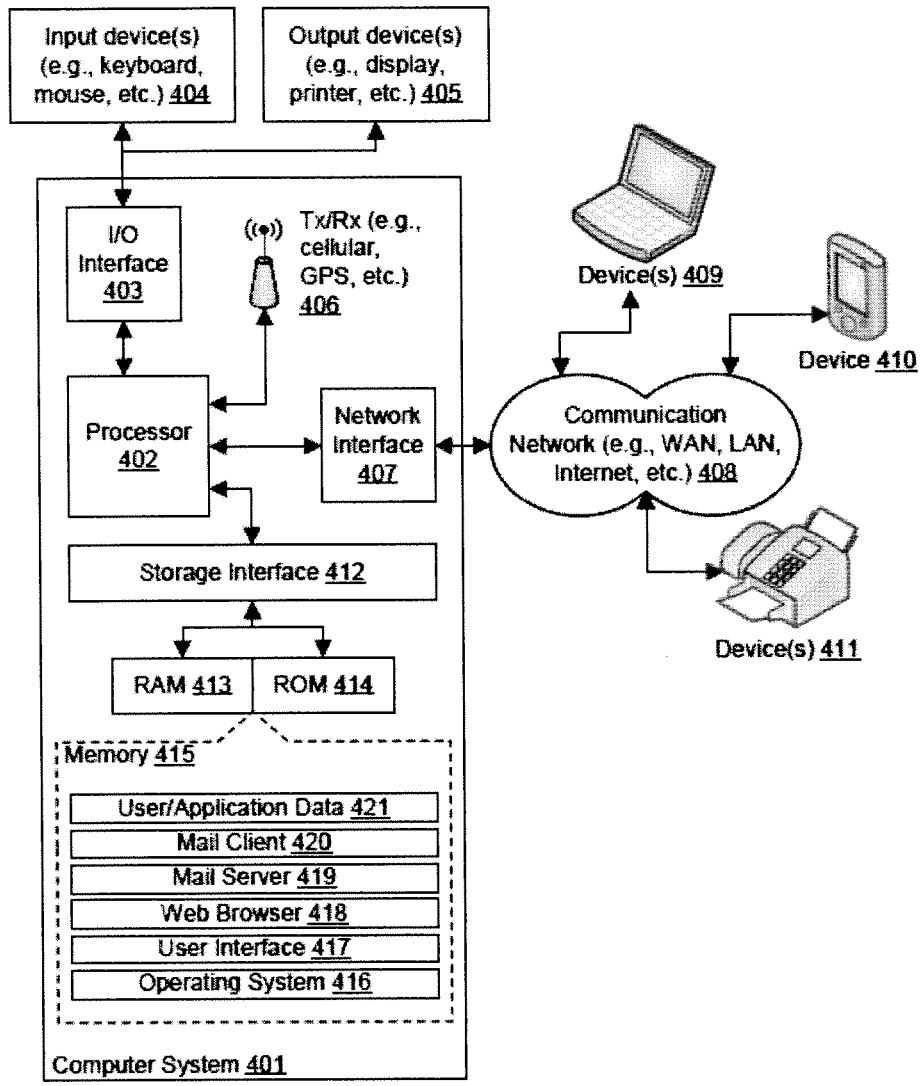
FIG. 4 is a block diagram of an exemplary computer system for implementing embodiments consistent with the present disclosure.

FIG. 4 is a block diagram of an exemplary computer system for implementing embodiments consistent with the present disclosure. Variations of computer system 401 may be used for implementing any of the devices presented in this disclosure. Computer system 401 may comprise a central processing unit ("CPU" or "processor") 402. Processor 402 may comprise at least one data processor for executing program components for executing user- or system-generated requests. A user may include a person, a person using a device such as those included in this disclosure, or such a device itself. The processor may include specialized processing units such as integrated system (bus) controllers, memory management control units, floating point units, graphics processing units, digital signal processing units, etc. The processor may include a microprocessor, such as AMD Athlon, Duron or Opteron, ARM's application, embedded or secure processors, IBM PowerPC, Intel's Core, Itanium, Xeon, Celeron or other line of processors, etc. The processor 302 may be implemented using mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), etc.

In some embodiments, processor 402 may be disposed in communication with one or more input/output (I/O) devices via I/O interface 403. The I/O interface 403 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using the I/O interface 03, the computer system 01 may communicate with one or more I/O devices. For example, the input device 404 may be an antenna, keyboard, mouse, joystick, (infrared), remote control, camera, card reader, fax machine, dongle, biometric reader, microphone, touch remote control, camera, card reader, fax machine, dongle, biometric reader, microphone, touch screen, touchpad, trackball, sensor (e.g., accelerometer, light sensor, GPS, gyroscope, proximity sensor, or the like), stylus, scanner, storage device, transceiver, video device/source, visors, etc. Output device 05 may be a printer, fax machine, video display (e.g., cathode ray tube (CRT), liquid crystal display (LCD), light-emitting diode (LED), plasma, or the like), audio speaker, etc. In some embodiments, a transceiver 06 may be disposed in connection with the processor 402. The transceiver may facilitate various types of wireless transmission or reception. For example, the transceiver may include an antenna operatively connected to a transceiver chip (e.g., Texas Instruments WiLink WL1283, Broadcom BCM4750IUB8, Infineon Technologies X-Gold 618-PMB9800, or the like), providing IEEE 802.11a/b/g/n, Bluetooth, FM, global positioning system (GPS), 2G/3G HSDPA/HSUPA communications, etc.

In some embodiments, the processor 402 may be disposed in communication with a communication network 408 via a network interface 407. The network interface 407 may communicate with the communication network 408. The network interface may employ connection protocols including, without limitation, direct connect, Ethernet (e.g., twisted pair 10/100/1000 Base T), transmission control protocol/internet protocol (TCP/IP), token ring, IEEE 802.11a/b/g/n/x, etc. The communication network 408 may include, without limitation, a direct interconnection, local area network (LAN), wide area network (WAN), wireless network (e.g., using Wireless Application Protocol), the Internet, etc. Using the network interface 07 and the communication network 408, the computer system 401 may communicate with devices 410, 411, and 412. These devices may include, without limitation, personal computer(s), server(s), fax machines, printers, scanners, various mobile devices such as cellular telephones, smartphones (e.g., Apple iPhone, Blackberry, Android-based phones, etc.), tablet computers, eBook readers (Amazon Kindle, Nook, etc.), laptop computers, notebooks, gaming consoles (Microsoft Xbox, Nintendo DS, Sony PlayStation, etc.), or the like. In some embodiments, the computer system 401 may itself embody one or more of these devices.

In some embodiments, the processor 402 may be disposed in communication with one or more memory devices (e.g., RAM 413, ROM 414, etc.) via a storage interface 412.

The storage interface may connect to memory devices including, without limitation, memory drives, removable disc drives, etc., employing connection protocols such as serial advanced technology attachment (SATA), integrated drive electronics (IDE), IEEE-1394, universal serial bus (USB), fiber channel, small computer systems interface (SCSI), etc. The memory drives may further include a drum, magnetic disc drive, magneto-optical drive, optical drive, redundant array of independent discs (RAID), solid-state memory devices, solid-state drives, etc.

The memory devices may store a collection of program or database components, including, without limitation, an operating system 416, user interface application 417, web browser 418, mail server 419, mail client 420, user/application data 421 (e.g., any data variables or data records discussed in this disclosure), etc. The operating system 416 may facilitate resource management and operation of the computer system 401. Examples of operating systems include, without limitation, Apple Macintosh OS X, Unix, Unix-like system distributions (e.g., Berkeley Software Distribution (BSD), FreeBSD, NetBSD, OpenBSD, etc.), Linux distributions (e.g., Red Hat, Ubuntu, Kubuntu, etc.), IBM OS/2, Microsoft Windows (XP, Vista/7/8, etc.), Apple iOS, Google Android, Blackberry OS, or the like. User interface 17 may facilitate display, execution, interaction, manipulation, or operation of program components through textual or graphical facilities. For example, user interfaces may provide computer interaction interface elements on a display system operatively connected to the computer system 401, such as cursors, icons, check boxes, menus, scrollers, windows, widgets, etc. Graphical user interfaces (GUIs) may be employed, including, without limitation, Apple Macintosh operating systems' Aqua, IBM OS/2, Microsoft Windows (e.g., Aero, Metro, etc.), Unix X-Windows, web interface libraries (e.g., ActiveX, Java, Javascript, AJAX, HTML, Adobe Flash, etc.), or the like.

In some embodiments, the computer system 401 may implement a web browser 418 stored program component. The web browser may be a hypertext viewing application, such as Microsoft Internet Explorer, Google Chrome, Mozilla Firefox, Apple Safari, etc. Secure web browsing may be provided using HTTPS (secure hypertext transport protocol), secure sockets layer (SSL), Transport Layer Security (TLS), etc. Web browsers may utilize facilities such as AJAX, DHTML, Adobe Flash, JavaScript, Java, application programming interfaces (APIs), etc. In some embodiments, the computer system 401 may implement a mail server 419 stored program component. The mail server may be an Internet mail server such as Microsoft Exchange, or the like. The mail server may utilize facilities such as ASP, ActiveX, ANSI C++/C#, Microsoft .NET, CGI scripts, Java, JavaScript, PERL, PHP, Python, WebObjects, etc. The mail server may utilize communication protocols such as internet message access protocol (IMAP), messaging application programming interface (MAPI), Microsoft Exchange, post office protocol (POP), simple mail transfer protocol (SMTP), or the like. In some embodiments, the computer system 401 may implement a mail client 420 stored program component. The mail client may be a mail viewing application, such as Apple Mail, Microsoft Entourage, Microsoft Outlook, Mozilla Thunderbird, etc.

In some embodiments, computer system 401 may store user/application data 421, such as, variables, records, etc. as described in this disclosure. Such databases may be implemented as fault-tolerant, relational, scalable, secure databases such as Oracle or Sybase. Alternatively, such databases may be implemented using standardized data structures, such as an array, hash, linked list, struct, structured text file (e.g., XML), table, or as object-oriented databases (e.g., using ObjectStore, Poet, Zope, etc.). Such databases may be consolidated or distributed, sometimes among the various computer systems discussed above in this disclosure. It is to be understood that the structure and operation of the any computer or database component may be combined, consolidated, or distributed in any working combination.

The specification has described a method and a system to reduce false alerts/alarms generated by the patient monitoring system 100, the false alerts/alarms being associated with clinical condition of the patient. The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments.

Furthermore, one or more non-transitory computer-readable storage media may be utilized in implementing embodiments consistent with the present disclosure. A non-transitory computer-readable storage medium refers to any type of physical memory on which information or data readable by a processor may be stored. Thus, a non-transitory computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

Other embodiments of the present disclosure will be apparent to those skilled in the art from consideration of the specification and practice of the embodiments disclosed herein. It is intended that the specification and examples be considered as exemplary only, with a true scope and spirit of the disclosure being indicated by the following claims.

What is claimed is:

1. A patient monitoring method, the method comprising:
    monitoring, by a patient monitoring apparatus, one or more clinical parameters associated with condition of a patient;
    identifying, by the patient monitoring apparatus, a clinical condition based on deviation of the monitored one or more clinical parameters from corresponding one or more first predefined criteria;
    determining, by the patient monitoring apparatus, a status associated with one or more devices that monitor the deviated one or more clinical parameters;
    generating, by the patient monitoring apparatus, a clinical alert based on the determined status not indicating an error by the one or more devices; and
    generating, by the patient monitoring apparatus, a machine alert based on the determined status indicating the error by the one or more devices, wherein the generated machine alert is rated per one or more defined conditions to determine an impact on the patient.

2. The method of claim 1, wherein the one or more clinical parameters comprise blood pressure, electrocardiography, heart rate, respiration rate, or body temperature.

3. The method of claim 1, wherein the clinical alert and the machine alert are represented visually and are different from each other.

4. The method of claim 1, further comprising monitoring, by the patient monitoring apparatus, one or more machine parameters associated with operation of the one or more devices.

5. The method of claim 4, wherein the determined status indicating the error by the one or more devices is based on deviation of the monitored one or more machine parameters from one or more second predefined criteria.

6. The method of claim 4, wherein the one or more machine parameters comprise electrical contacts, a battery in the one or more devices, signal to noise (SNR) ratio, or connectivity.

7. A patient monitoring system, the system comprising:
    at least one processor;
    at least one memory coupled to the at least one processor, the at least one memory storing processor executable instructions which when executed by the at least one processor causes the at least one processor to:
        instruct each of one or more devices, in communication with the processor, to monitor an associated clinical parameter;
        identify a clinical condition of a patient based on deviation of the monitored one or more clinical parameters from a corresponding one or more first predefined criteria;
        determine a status associated with each of the one or more devices monitoring the deviated one or more clinical parameters;
        generate a clinical alert based on the status not indicating an error by the one or more devices; and generate a machine alert based on the determined status indicating the error by the one or more devices, wherein the generated machine alert is rated per one or more defined conditions to determine an impact on the patient.

8. The system of claim 7, wherein the one or more clinical parameters comprise blood pressure, electrocardiography, heart rate, respiration rate, or body temperature.

9. The system of claim 7, wherein the clinical alert and the machine alert are represented visually and are different from each other.

10. The system of claim 9, wherein the clinical alert and the machine alert are displayed on a display.

11. The system of claim 9, wherein the status indicating the error by the one or more devices is based on deviation of one or more machine parameters from a corresponding one or more second predefined criteria associated with operation of the one or more devices.

12. The system of claim 11, wherein the one or more machine parameters comprise electrical contacts, a battery in the one or more devices, signal to noise (SNR) ratio, or connectivity.

13. The system of claim 11, wherein the memory stores the one or more first predefined criteria and the one or more second predefined criteria.

14. A non-transitory computer readable medium having stored thereon instructions for monitoring a patient comprising executable code which when executed by a processor, causes the processor to perform steps:

monitoring one or more clinical parameters associated with condition of a patient;

identifying a clinical condition based on deviation of the monitored one or more clinical parameters from corresponding one or more first predefined criteria;

determining a status associated with one or more devices that monitor the deviated one or more clinical parameters;

generating a clinical alert based on the determined status not indicating an error by the one or more devices; and generating a machine alert based on the determined status indicating the error by the one or more devices, wherein the generated machine alert is rated per one or more defined conditions to determine an impact on the patient.

15. The medium of claim 14, wherein the one or more clinical parameters comprise blood pressure, electrocardiography, heart rate, respiration rate, or body temperature.

16. The medium of claim 14, wherein the clinical alert and the machine alert are represented visually and are different from each other.

17. The medium of claim 16, further comprising monitoring one or more machine parameters associated with operation of the one or more devices.

18. The medium of claim 17, wherein the determined status indicating the error by the one or more devices is based on deviation of the monitored one or more machine parameters from one or more second predefined criteria.

19. The medium of claim 17, wherein the one or more machine parameters comprise electrical contacts, a battery in the one or more devices, signal to noise (SNR) ratio, or connectivity.

* * * * *